United States Patent
Lockhart et al.

(10) Patent No.: US 11,110,241 B2
(45) Date of Patent: Sep. 7, 2021

(54) FABRIC CUSHION MEMBER

(71) Applicant: KONINKLIJKE PHILIPS N.V., Eindhoven (NL)

(72) Inventors: Harold Allen Lockhart, Mt Pleasant, PA (US); Derrick Blake Andrews, Markleton, PA (US)

(73) Assignee: Koninklijke Philips N.V., Eindhoven (NL)

( * ) Notice: Subject to any disclaimer, the term of this patent is extended or adjusted under 35 U.S.C. 154(b) by 358 days.

(21) Appl. No.: 16/084,577

(22) PCT Filed: Mar. 8, 2017

(86) PCT No.: PCT/IB2017/051344
§ 371 (c)(1),
(2) Date: Sep. 13, 2018

(87) PCT Pub. No.: WO2017/158471
PCT Pub. Date: Sep. 21, 2017

(65) Prior Publication Data
US 2019/0070379 A1    Mar. 7, 2019

Related U.S. Application Data

(60) Provisional application No. 62/307,624, filed on Mar. 14, 2016.

(51) Int. Cl.
*A61M 16/06* (2006.01)

(52) U.S. Cl.
CPC ........ *A61M 16/0622* (2014.02); *A61M 16/06* (2013.01); *A61M 16/0616* (2014.02);
(Continued)

(58) Field of Classification Search
CPC ..... A41D 3/08; A61M 16/0057; A61M 16/06; A61M 16/0605; A61M 16/0616;
(Continued)

(56) References Cited

U.S. PATENT DOCUMENTS 4,303,712 A * 12/1981 Woodroof ............. B29C 65/483
428/58
6,277,469 B1 * 8/2001 Wildeman ................ B32B 5/06
428/167

(Continued)

FOREIGN PATENT DOCUMENTS

| CN | 101951984 A | 1/2011 |
|---|---|---|
| DE | 102009038655 A1 | 2/2011 |

(Continued)

*Primary Examiner* — Annette Dixon
(74) *Attorney, Agent, or Firm* — Michael W. Haas

(57) ABSTRACT

A cushion member (100, 200) for a patient interface device (4) that includes a sealing portion (110, 210) having a flap portion (111, 211) including a first layer (116, 216) and a second layer (118, 218) mechanically bonded to the first layer. The first layer is structured to engage a face of a patient and is made of a fabric material. The second layer is made of a material selected from the group consisting of a monomer, a polymer, and a mixture of a monomer and a (Continued)

polymer. A base portion (170, 270) is bonded to the second layer. The base portion is structured to be coupled to a gas delivery conduit (8).

14 Claims, 14 Drawing Sheets

(52) U.S. Cl.
CPC . *A61M 16/0683* (2013.01); *A61M 2205/0216* (2013.01); *A61M 2205/0238* (2013.01); *A61M 2207/00* (2013.01)

(58) Field of Classification Search
CPC .......... A61M 16/0622; A61M 16/0633; A61M 16/0666; A61M 16/0683; A61M 16/1055; A61M 16/107; A61M 16/1075; A61M 16/16; A61M 16/161; A61M 16/208; A61M 2016/0027; A61M 2016/0036; A61M 2205/02; A61M 2205/0205; A61M 2205/0216; A61M 2205/0222; A61M 2205/0238; A61M 2205/3368; A61M 2205/7536; A61M 2207/10; A61M 2210/0618; B29C 51/082; B29C 51/14; B29C 51/32; B29C 70/345; B29K 2083/00; B29K 2105/256; B29L 2031/753; B29L 2274/00; B29L 2307/546; B32B 2307/56; B32B 2307/7246; B32B 2307/7265; B32B 2307/744; B32B 25/042; B32B 25/10; B32B 25/20; B32B 2535/00; B32B 3/266; B32B 3/28; B32B 5/024; B32B 5/026; B32B 5/04; B32B 5/06; B32B 5/22; B32B 5/26; Y10T 428/2457; Y10T 428/24612; Y10T 442/637; Y10T 442/659
See application file for complete search history.

(56) References Cited

U.S. PATENT DOCUMENTS

| | | | |
|---|---|---|---|
| 10,183,137 | B2 | 1/2019 | Chodkowski et al. |
| 2004/0221850 | A1* | 11/2004 | Ging .................. A61M 16/0683 128/206.27 |
| 2005/0205096 | A1 | 9/2005 | Matula, Jr. |
| 2010/0146680 | A1* | 6/2010 | Cuoco ...................... A41D 3/08 2/84 |
| 2010/0258136 | A1 | 10/2010 | Doherty |
| 2012/0080035 | A1 | 4/2012 | Guney |
| 2014/0000616 | A1 | 1/2014 | Haibach |
| 2014/0109911 | A1* | 4/2014 | Asvadi .............. A61M 16/0057 128/205.25 |
| 2014/0251338 | A1* | 9/2014 | Asvadi .............. A61M 16/0633 128/206.22 |
| 2015/0151071 | A1 | 6/2015 | Eves |
| 2017/0049983 | A1* | 2/2017 | Ellis .......................... B32B 5/26 |
| 2017/0326320 | A1* | 11/2017 | Baigent ............. A61M 16/0683 |
| 2020/0114107 | A1* | 4/2020 | Guney .............. A61M 16/0616 |

FOREIGN PATENT DOCUMENTS

| | | | |
|---|---|---|---|
| EP | 2808050 | A2 | 3/2014 |
| JP | 2015020044 | A | 2/2015 |
| KR | 20130087450 | A | 8/2013 |
| TW | 201018415 | A | 5/2010 |
| WO | WO2013001419 | A1 | 1/2013 |
| WO | WO2013001438 | A1 | 1/2013 |
| WO | WO2013006913 | A1 | 1/2013 |
| WO | WO2015063283 | A1 | 5/2015 |
| WO | PCT/US2015/000041 | * | 10/2015 |
| WO | WO2015147947 | A2 | 10/2015 |
| WO | PCT/AU2015/050745 | * | 6/2016 |

\* cited by examiner

FABRIC CUSHION MEMBER

CROSS-REFERENCE TO RELATED APPLICATIONS

This patent application claims the priority benefit under 35 U.S.C. § 371 of international patent application no. PCT/IB02017/051344, filed Mar. 8, 2017, which claims the priority benefit under 35 U.S.C. § 119(e) of U.S. Provisional Application No. 62/307,624, filed on Mar. 14, 2016, the contents of which are herein incorporated by reference.

BACKGROUND OF THE INVENTION

1. Field of the Invention

The present invention relates to non-invasive ventilation and pressure support systems wherein a patient interface device is used to deliver a flow of breathing gas to a patient, and in particular to cushion members for such patient interface devices. The present invention is also related to methods of manufacturing cushion members.

2. Description of the Related Art

There are numerous situations where it is necessary or desirable to deliver a flow of breathing gas non-invasively to the airway of a patient, i.e., without intubating the patient or surgically inserting a tracheal tube in their esophagus. For example, it is known to ventilate a patient using a technique known as non-invasive ventilation. It is also known to deliver positive airway pressure (PAP) therapy to treat certain medical disorders, the most notable of which is obstructive sleep apnea (OSA). Known PAP therapies include continuous positive airway pressure (CPAP), wherein a constant positive pressure is provided to the airway of the patient in order to splint open the patient's airway, and variable airway pressure, wherein the pressure provided to the airway of the patient is varied with the patient's respiratory cycle. Such therapies are typically provided to the patient at night while the patient is sleeping.

Non-invasive ventilation and pressure support therapies as just described involve a gas flow generator to produce a flow of breathing gas, and the placement of a patient interface device including a mask component on the face of a patient. The gas flow generator produces positive air pressure by taking air in from the surroundings and spinning a fan to push the air out of the machine, through a delivery conduit, and into the patient interface device to be delivered to the patient.

Traditional cushion members for patient interface devices include a sealing portion that is structured to engage the face of the patient in order to provide a seal therewith. Known sealing portions suffer from a number of drawbacks, such as applying too much pressure to certain areas of the face, resulting in red marks and a decreased ability of the patient to make an emotional connection with the patient interface device. Furthermore, current injection molding techniques limit the ability to incorporate thin films in the sealing portions. Additionally, in known sealing portions that are made of fabric materials, gas flow leaks often occur as a result of the stitching between the fabric and the body of the cushion member. Moreover, employing a sealing portion entirely constructed of a fabric material is generally not practicable, as current fabric materials do not allow gas impermeability.

SUMMARY OF THE INVENTION

Accordingly, it is an object of the present invention to provide a cushion member for a patient interface device. The cushion member includes: a sealing portion having a flap portion including a first layer and a second layer mechanically bonded to the first layer, the first layer being structured to engage a face of a patient and being made of a fabric material, the second layer being made of a material selected from the group consisting of a monomer, a polymer, and a mixture of a monomer and a polymer, and a base portion bonded to the second layer, the base portion being structured to be coupled to a gas delivery conduit.

It is yet another object of the present invention to provide a method of manufacturing a cushion member for a patient interface device. The cushion member includes a sealing portion and a base portion. The base portion is structured to be coupled to a gas delivery conduit. The sealing portion has a flap portion. The method includes the steps of: mechanically bonding a first layer of the flap portion to a second layer of the flap portion, the first layer being structured to engage a face of a patient and being made of a fabric material, the second layer being made of a material selected from the group consisting of a monomer, a polymer, and a mixture of a monomer and a polymer, and bonding the base portion to the second layer.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

Figure 1:
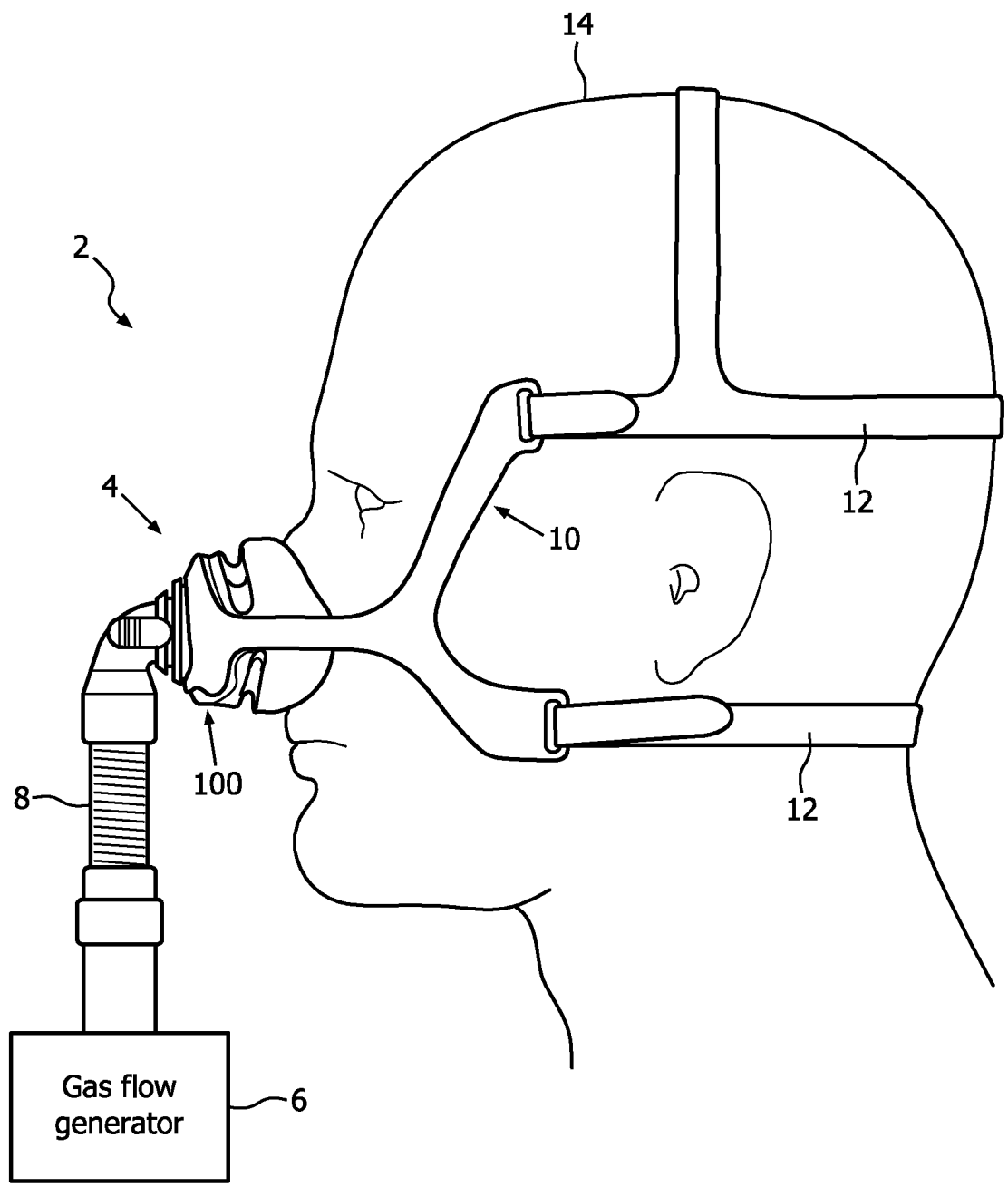
FIG. 1 is a side view of a cushion member, shown as employed in a pressure support system and on a patient, in accordance with a non-limiting embodiment of the disclosed concept.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As employed herein, the statement that two or more parts or components "engage" one another shall mean that the parts exert a force against one another either directly or through one or more intermediate parts or components. As employed herein, the term "number" shall mean one or an integer greater than one (i.e., a plurality). Directional phrases used herein, such as, for example and without limitation, left, right, upper, lower, front, back, on top of, and derivatives thereof, relate to the orientation of the elements shown in the drawings and are not limiting upon the claims unless expressly recited therein.

As used herein, the term "fabric" shall mean a material consisting of a network of interlaced or otherwise entangled natural or artificial fibers made by, for example and without limitation, weaving, knitting, spreading, crocheting, or bonding (e.g., by chemical, mechanical, heat or solvent treatment) the fibers to form the network, and may include, for example, and without limitation, woven and nonwoven fabric materials.

As used herein, the phrase "mechanical bond" shall mean a bond formed as a result of the curing (i.e., solidifying) of a material selected from the group consisting of a monomer, a polymer, and a mixture of a monomer and a polymer (e.g., without limitation, silicone) to a fabric material. For example and without limitation, a bond formed when a viscous silicone material flows into fibers of a fabric material and is thereafter cured is a mechanical bond. A connection formed when a fabric material is stitched to a silicone material is not a mechanical bond.

As used herein, the phrase "chemical bond" shall mean a bond formed as a result of the curing (i.e., solidifying) of a first material to a second material, where each of the first and second materials is made of a monomer, a polymer, or a mixture of a monomer and a polymer.

FIG. 1 shows a pressure support system 2 in accordance with a non-limiting exemplary embodiment of the disclosed concept. Pressure support system 2 has a patient interface device 4, a gas flow generator 6, and a gas delivery conduit (e.g., hose 8) structured to fluidly couple gas flow generator 6 to patient interface device 4. Patient interface device 4 includes a frame member 10, a number of strap members 12 coupled to frame member 10, and a cushion member 100 coupled to frame member 10. As shown, frame member 10 and strap members 12 together allow cushion member 100 to be secured against a face of a patient 14 in order to communicate a flow of breathing gas from gas flow generator 6 to patient 14.

Figure 2:
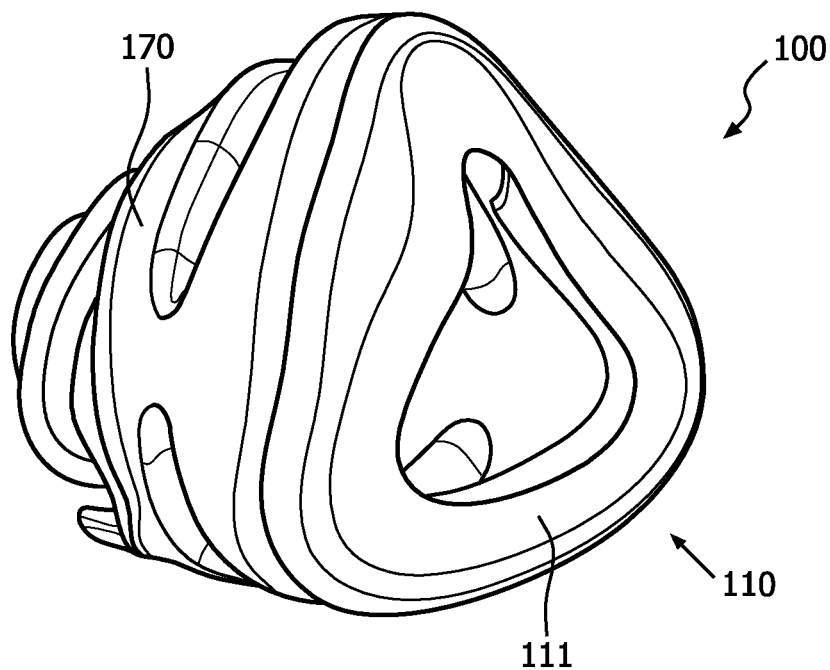
FIGS. 2 and 3 are isometric and exploded views, respectively, of the cushion member of FIG. 1.
Figure 3:
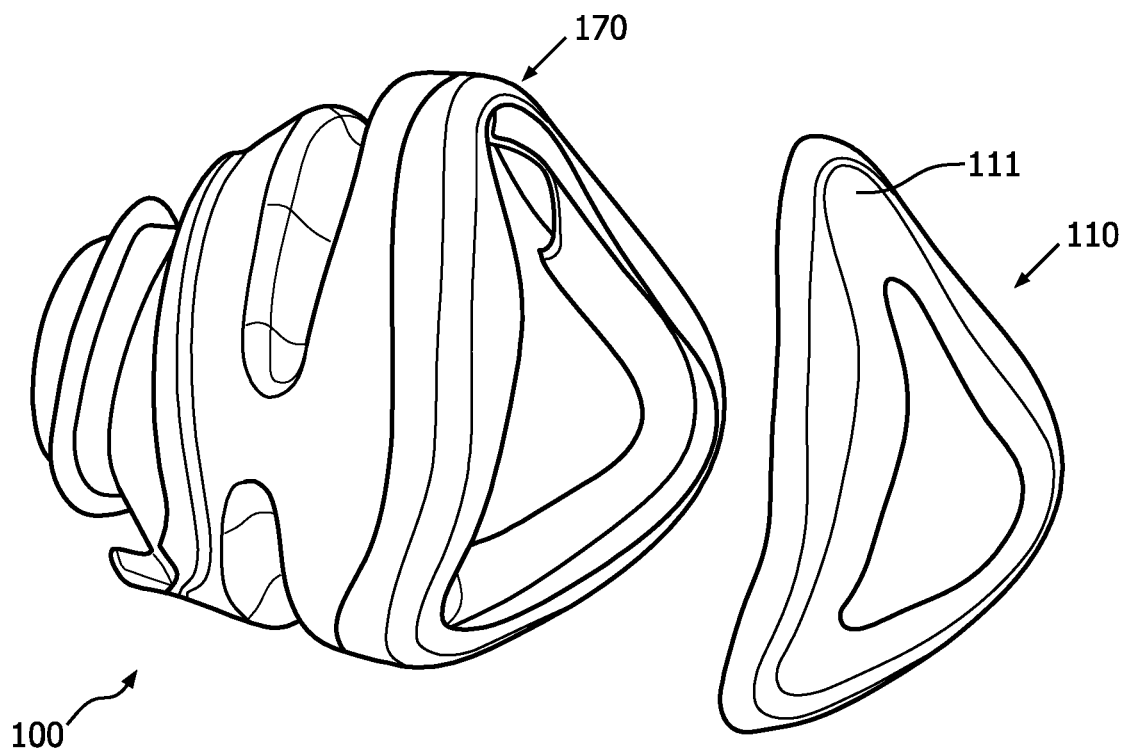
Figure 4:
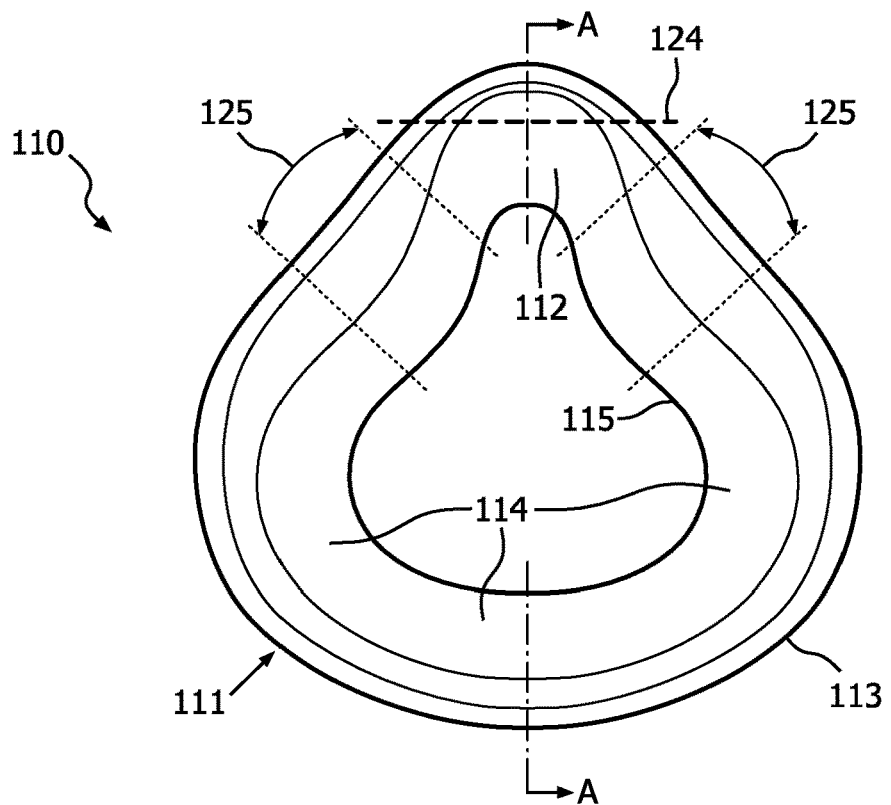
FIG. 4 is a bottom view of a flap portion for the cushion member of FIG. 1.

As shown in FIGS. 2 and 3, cushion member 100 includes a sealing portion 110 and a base portion 170. Base portion 170 is structured to be coupled to hose 8 (FIG. 1). In the depicted embodiment, sealing portion 110 is a flexible flap portion 111. Referring to FIG. 4, flap portion 111 has a nose bridge portion 112, a pair of opposing nasal transition portions 125 each extending from nose bridge portion 112, a body portion 114 connecting nasal transition portions 125 to one another, an outer edge 113, and an inner edge 115.

Figure 5:
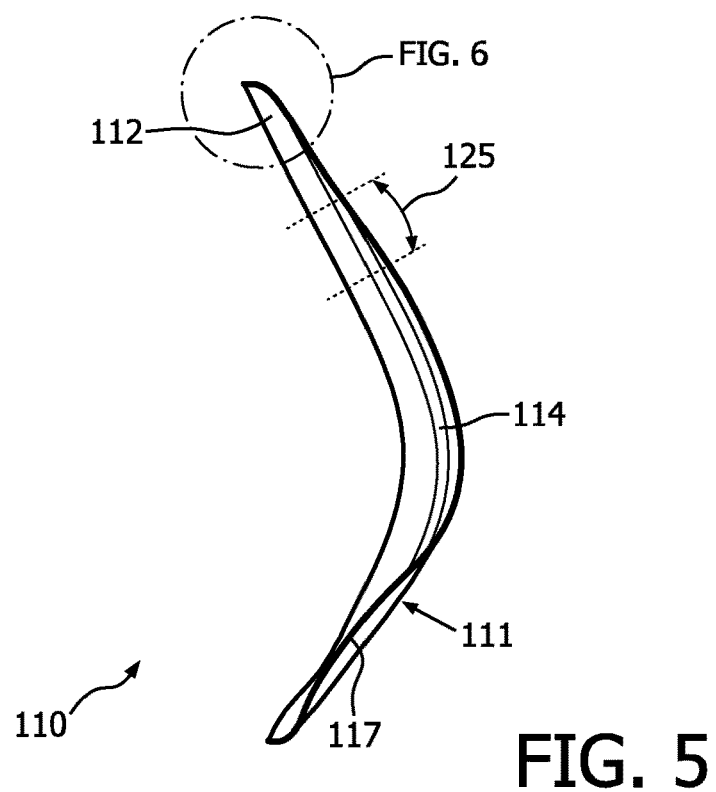
FIG. 5 is a section view of the flap portion of FIG. 4, taken along line A A of FIG. 4.
Figure 6:
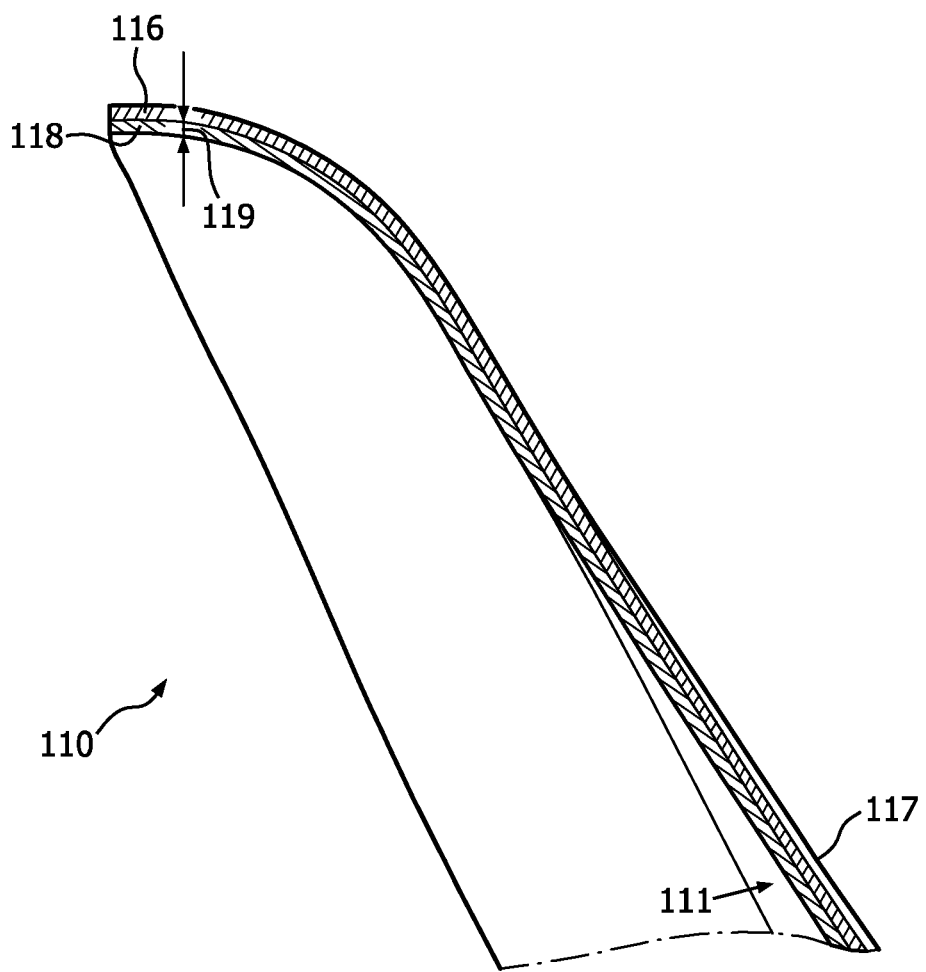
FIG. 6 is an enlarged view of a portion of the flap portion of FIG. 5.

FIG. 5 shows a section view of flap portion 111 and FIG. 6 shows an enlarged view of a portion of FIG. 5. As shown in FIG. 6, flap portion 111 includes a first layer 116 and a second layer 118. First layer 116 is made of a fabric material having single or multiple stretch directions (e.g., without limitation, a fabric material including spandex and/or lycra). Second layer 118 is made of a monomer, a polymer, or a mixture of a monomer and a polymer (e.g., without limitation, silicone). Second layer 118 is mechanically bonded to and overlays (i.e., is located on top of) first layer 116. For example and without limitation, during manufacture, second layer 118 may be applied to first layer 116 as a viscous semi-liquid (e.g., heated to a temperature well below the fabric color set temperature of first layer 116, but high enough to allow for a proper cure) before molding of base portion 170 occurs. Additionally, the mechanical bond is structured such that second layer 118 partially extends into first layer 116. That is, during manufacture, the room temperature viscous semi-liquid second layer 118 flows into the fabric fibers of first layer 116 through a minimal exertion of pressure prior to establishing a proper cure. However, second layer 118 advantageously does not extend entirely through first layer 116. In this manner, flap portion 111 advantageously has an external engaging surface 117 that is made of the material of first layer 116.

Stated differently, first layer 116, via engaging surface 117, is structured to engage the face of patient 14 (FIG. 1) and second layer 118 is not structured to engage the face of patient 14. The inventors have discovered that a relatively large proportion of patients prefer the feel of a fabric material, such as a fabric material including spandex and/or lycra in the construction, against the face as opposed to traditional silicone sealing materials. As a result, having first layer 116 engage the face of patient 14 advantageously improves the comfort and emotional connection between these patients and patient interface device 4. Moreover, the mechanical bond between first and second layers 116,118 advantageously provides for a relatively strong seal. That is, unlike prior art sealing portions (not shown) that include fabric materials, which suffer from leaks due to the stitching between the fabric and silicone portions, the mechanical bond between first and second layers 116,118 significantly reduces the potential for leaks. As such, first layer 116 operates to provide comfort and emotional connection to patient 14, while second layer 118 operates to provide a gas impermeable structure, thereby allowing flap portion 111 to properly function as a sealing element.

First layer 116 also has a density of between 100 and 350 grams per square meter, and has wicking properties that significantly improve the ability to remove moisture buildup against the skin, as compared to prior art silicone sealing portions. Continuing to refer to FIG. 6, second layer 118 has a thickness 119 of between 0.002 and 0.02 inches, which is significantly less than traditional prior art injection molded silicone sealing portions. The density and moisture wicking properties of first layer 116, combined with the relatively small thickness of second layer 118, together advantageously aid in the reduction of red marks by reducing shear loads on facial features generated while patient interface device 4 is donned by patient 14.

Moreover, first layer 116 may be a single or multidirectional stretch material. That is, the primary direction of stretch of first layer 116 (i.e., the direction along which first layer 116 is structured to resist tensile forces the least) may be in a single direction or in multiple directions. Referring to FIG. 4, first layer 116 has a single stretch direction on an axis 124 (i.e., perpendicular to a longitudinal axis of a primary nose bone of patient 14) across nose bridge portion 112, thereby further allowing flap portion 111 to reduce shear loads and red marks on patient 14 proximate nose bridge portion 112. However, it will be appreciated that a similar suitable alternative flap portion (not shown) may have different stretch characteristics, without departing from the scope of the disclosed concept. For example and without limitation, it is within the scope of the disclosed concept for the primary direction of stretch of a first layer to be perpendicular to axis 124 (i.e., a direction parallel to a longitudinal axis of a primary nose bone of patient 14), a construction which provides advantageous improvements in terms of ability to create a seal, comfort level, and stability.

Figure 7A:
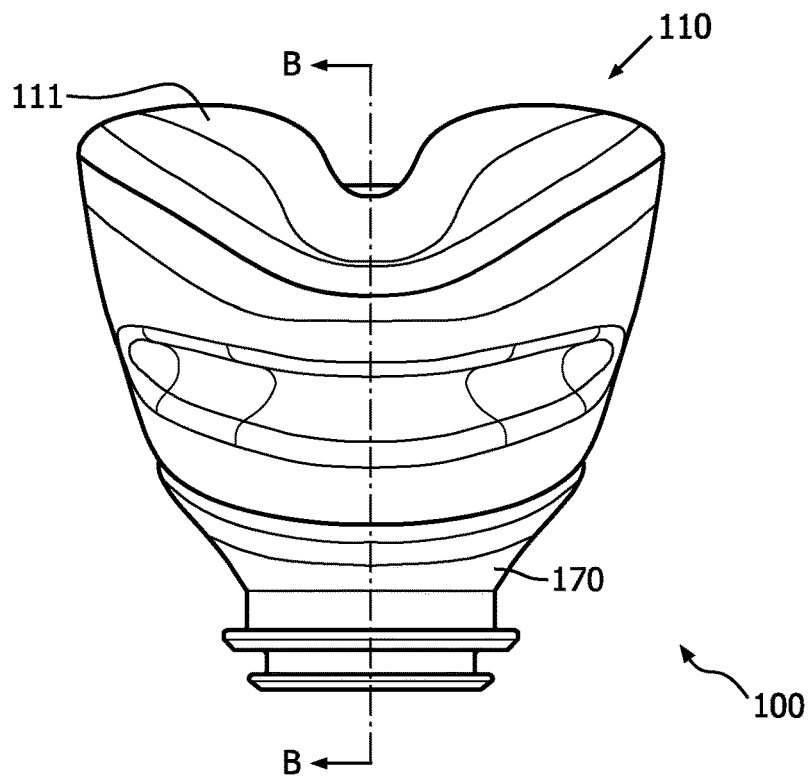
FIG. 7A is another view of the cushion member of FIG. 1.
Figure 7B:
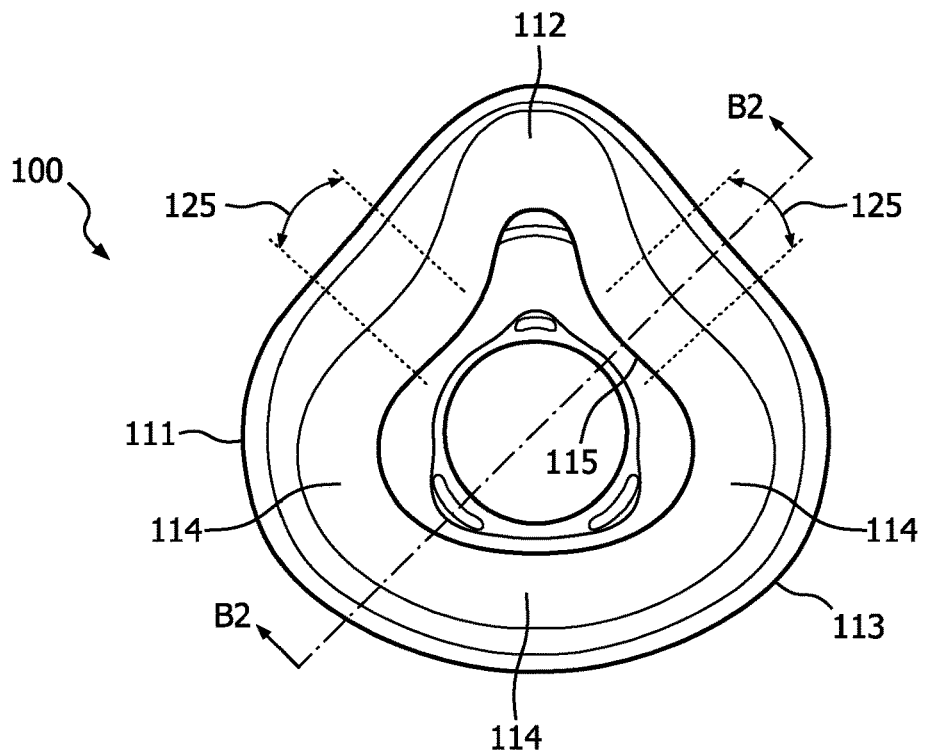
FIG. 7B is another view of the cushion member of FIG. 1.
Figure 8A:
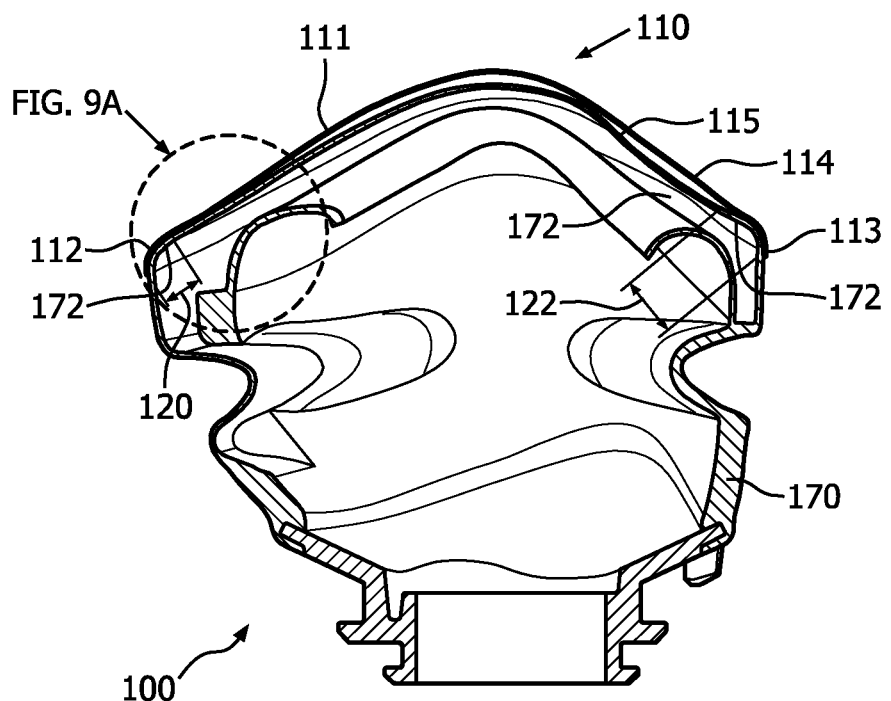
FIG. 8A is a section view of the cushion member of FIG. 7A, taken along line B-B of FIG. 7A.
Figure 8B:
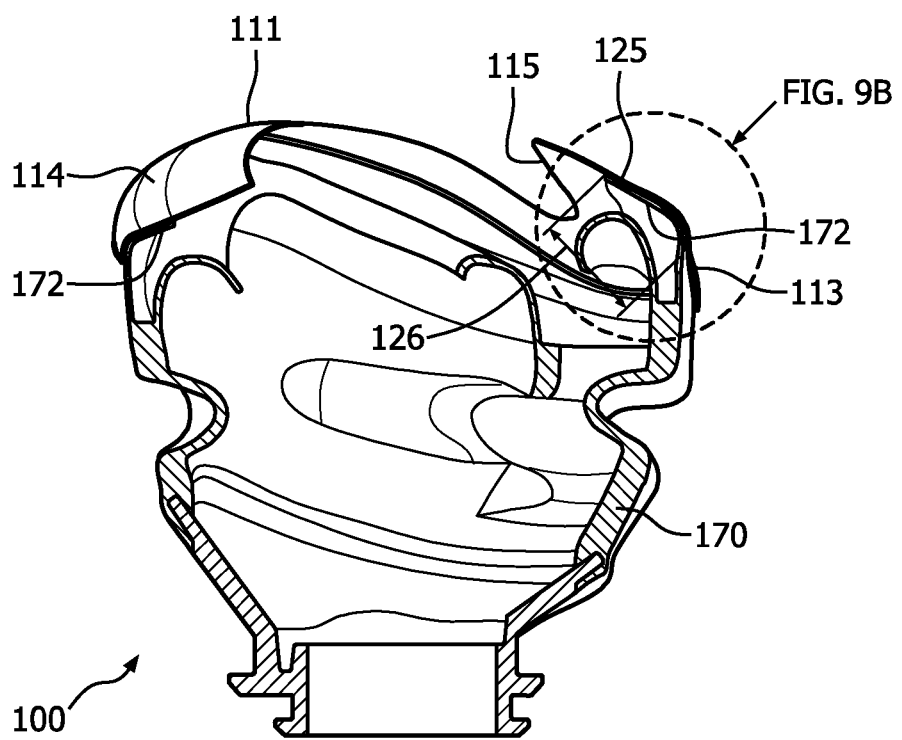
FIG. 8B is a section view of the cushion member of FIG. 7B, taken along line B2-B2 of FIG. 7B.
Figure 9A:
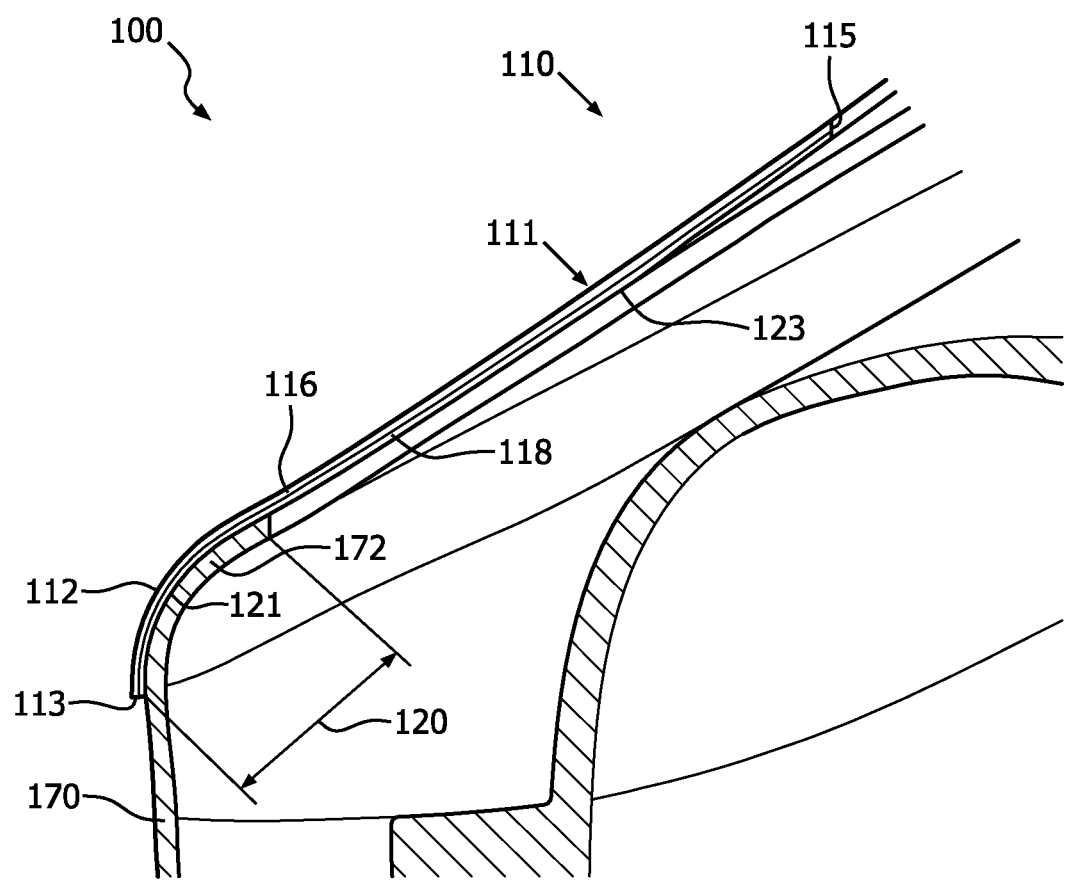
FIG. 9A is an enlarged view of a portion of the cushion member of FIG. 8A.
Figure 9B:
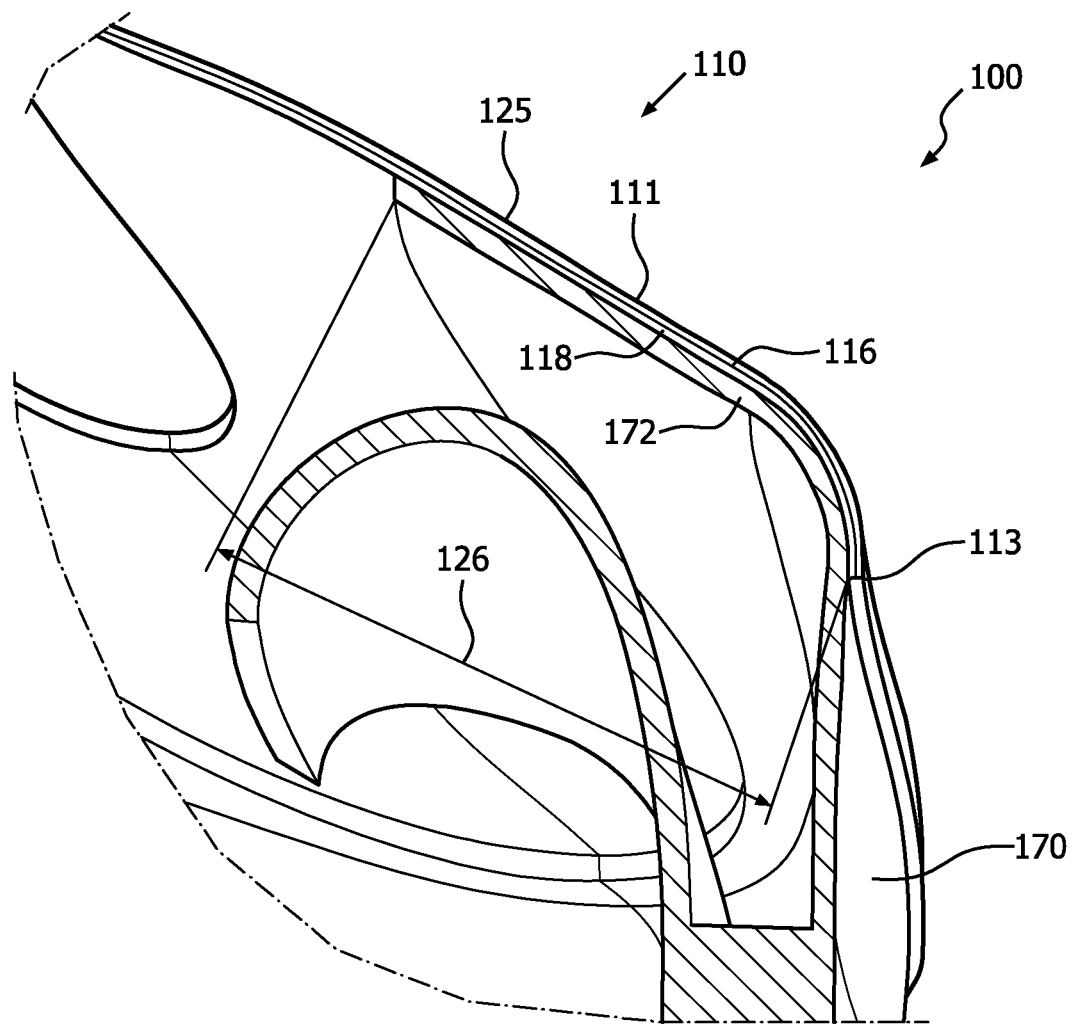
FIG. 9B is an enlarged view of a portion of the cushion member of FIG. 8B.

FIG. 7A shows another view of cushion member 100 and FIG. 8A shows a section view of FIG. 7A. As shown in FIG. 8A, base portion 170 includes a bonding layer 172. Referring to the enlarged view of FIG. 9A, bonding layer 172 is chemically bonded to second layer 118 to form a lap-joint. In addition to functioning as a relatively strong bond between base portion 170 and second layer 118, the lap joint advantageously provides a sufficient amount of stiffness to flap portion 111 to prevent buckling (i.e., flutter). As shown, bonding layer 172 is located between outer edge 113 and inner edge 115 and extends inwardly from outer edge 113 of nose bridge portion 112 a first distance 120. Referring again to FIG. 8A, bonding layer 172 extends inwardly from outer edge 113 of body portion 114 a second distance 122 greater than first distance 120. In this manner, cushion member 100 is advantageously structured to allow for further flexibility proximate nose bridge portion 112. Additionally, referring to FIGS. 8B and 9B, which are section views of FIG. 7B, bonding layer 172 extends inwardly from outer edge 113 of nasal transition portions 125 a third distance 126 greater than first distance 120 and second distance 122. As a result, flap portion 111 is advantageously able to lay properly against the sides of the nose of patient 14 to maintain a seal and eliminate flutter in this area.

More specifically, locations where flap portion 111 is bonded to bonding layer 172 are structured to resist tensile forces more (i.e., are more stiff) than locations where flap portion 111 is not bonded to bonding layer 172. By having bonding layer 172 extend inwardly from outer edge 113 a smaller distance proximate nose bridge portion 112 than at body portion 114 (i.e., by having a greater proportion of flap portion 111 not be bonded to bonding layer 172 proximate nose bridge portion 112 as compared to body portion 114), flap portion 111 is advantageously structured to resist tensile forces (i.e., forces applied by the nose of patient 14) less proximate nose bridge portion 112 than at body portion 114.

As a result, flap portion 111 is able to stretch (i.e., deflect) a greater amount proximate nose bridge portion 112 as compared to body portion 114. This is desirable because of the rigidity associated with the nose bone of patient 14. That is, having increased flexibility proximate nose bridge portion 112 increases comfort for patient 14 and reduces the likelihood of red mark formation.

Referring again to FIG. 9A, second layer 118 includes a first portion 121 and a second portion 123 extending from first portion 121. First portion 121 is chemically bonded to bonding layer 172 and second portion 123 is not chemically bonded to bonding layer 172. As shown, second portion 123 is generally flat. This is distinct from typical prior art sealing portions, which are not flat, but rather have concave internal portions. It will be appreciated that the instant redefined profile of flap portion 111 advantageously prevents wrinkles and/or excessive stretching of flap portion 111 when base portion 170 is molded onto flap portion 111 via bonding layer 172 at the lap-joint. That is, prior art sealing portion profiles would result in undesirable wrinkles or stretching if employed with a flap portion made of similar materials as flap portion 111. Additionally, the disclosed redefined profile provides greater contact area between cushion member 100 and the face of patient 14 as compared to prior art sealing portions in order to maintain proper functionality of patient interface device 4. Accordingly, when cushion member 100 is not donned by patient 14, flap portion 111 is generally not in a state of tension. Thus, when cushion member 100 is donned by patient 14 and flap portion 111 engages the face of patient 14, flap portion 111 is able to conform to the facial features of patient 14 without exerting a significantly large biasing force, as compared to prior art sealing portions.

Figure 10:
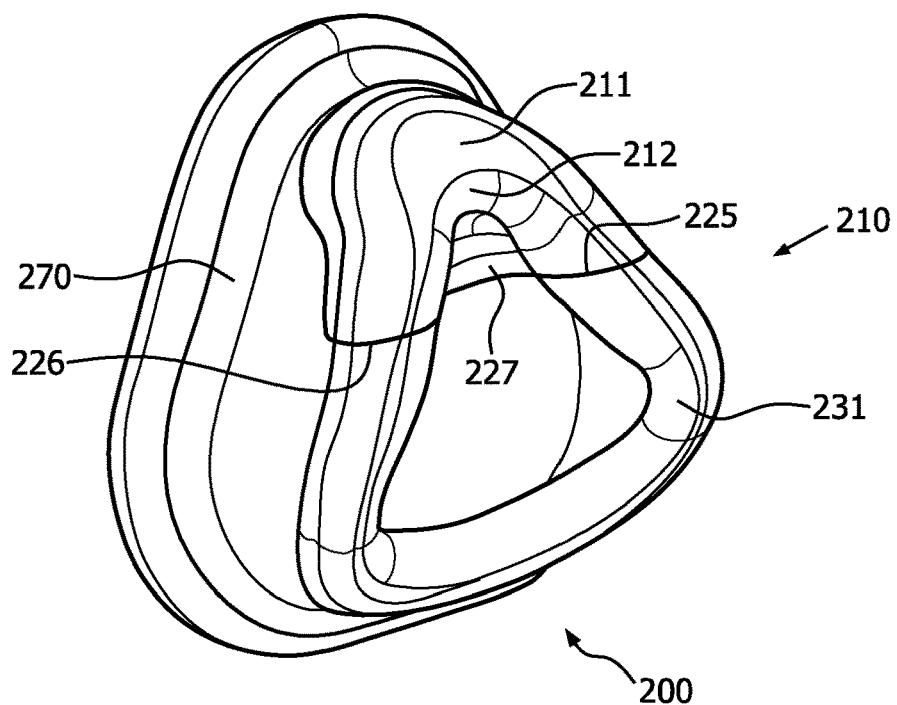
FIGS. 10, 11, and 12 are isometric, top plan, and exploded views, respectively, of another cushion member, in accordance with an alternative embodiment of the disclosed concept.
Figure 11:
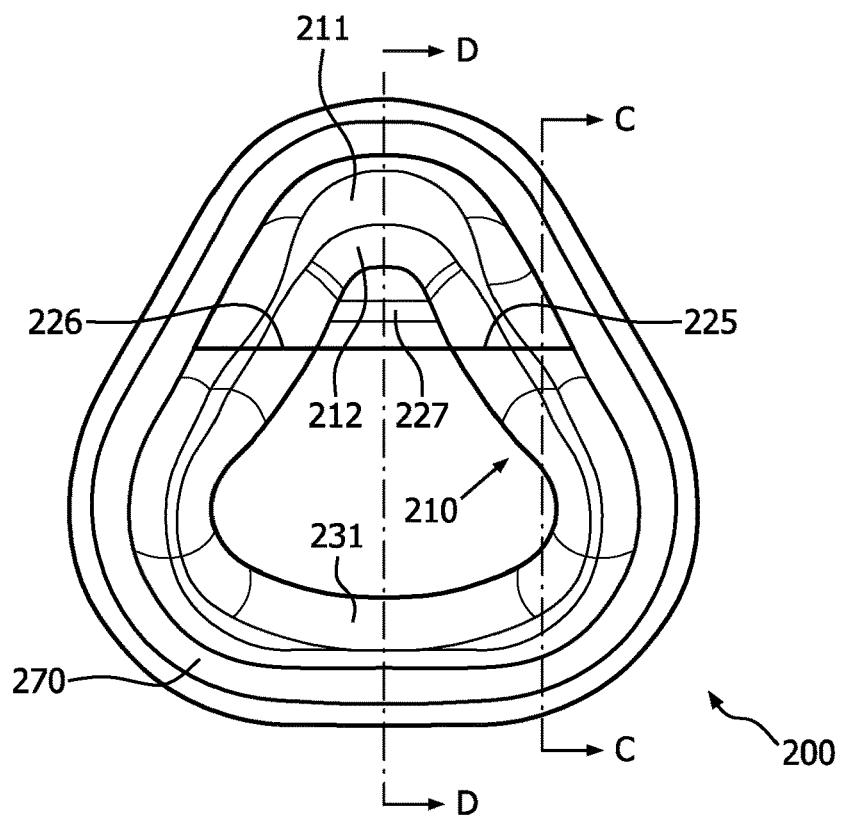
Figure 12:
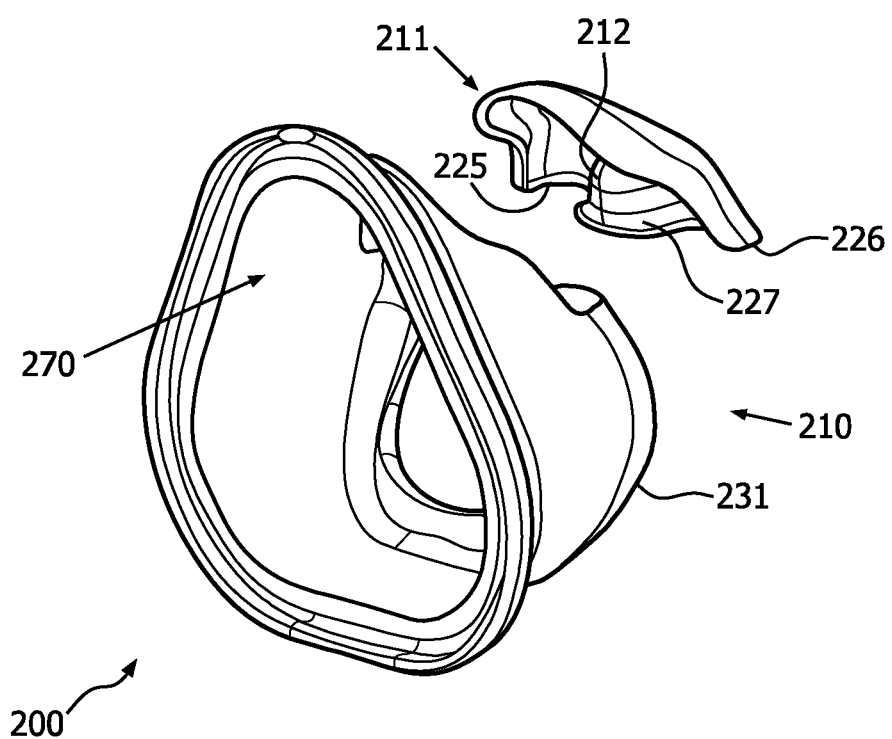

FIGS. 10, 11, and 12 show front isometric, top plan, and exploded views, respectively, of full face cushion member 200 that may be implemented in patient interface device 4 instead of cushion member 100, in accordance with an alternative non-limiting embodiment of the disclosed concept. Cushion member 200 includes a sealing portion 210 and a base portion 270. Sealing portion 210 has a first flap portion 211 and a second flap portion 231. First flap portion 211 has a first bonding portion 225 and a second bonding portion 226 located opposite first bonding portion 225.

Figure 13:
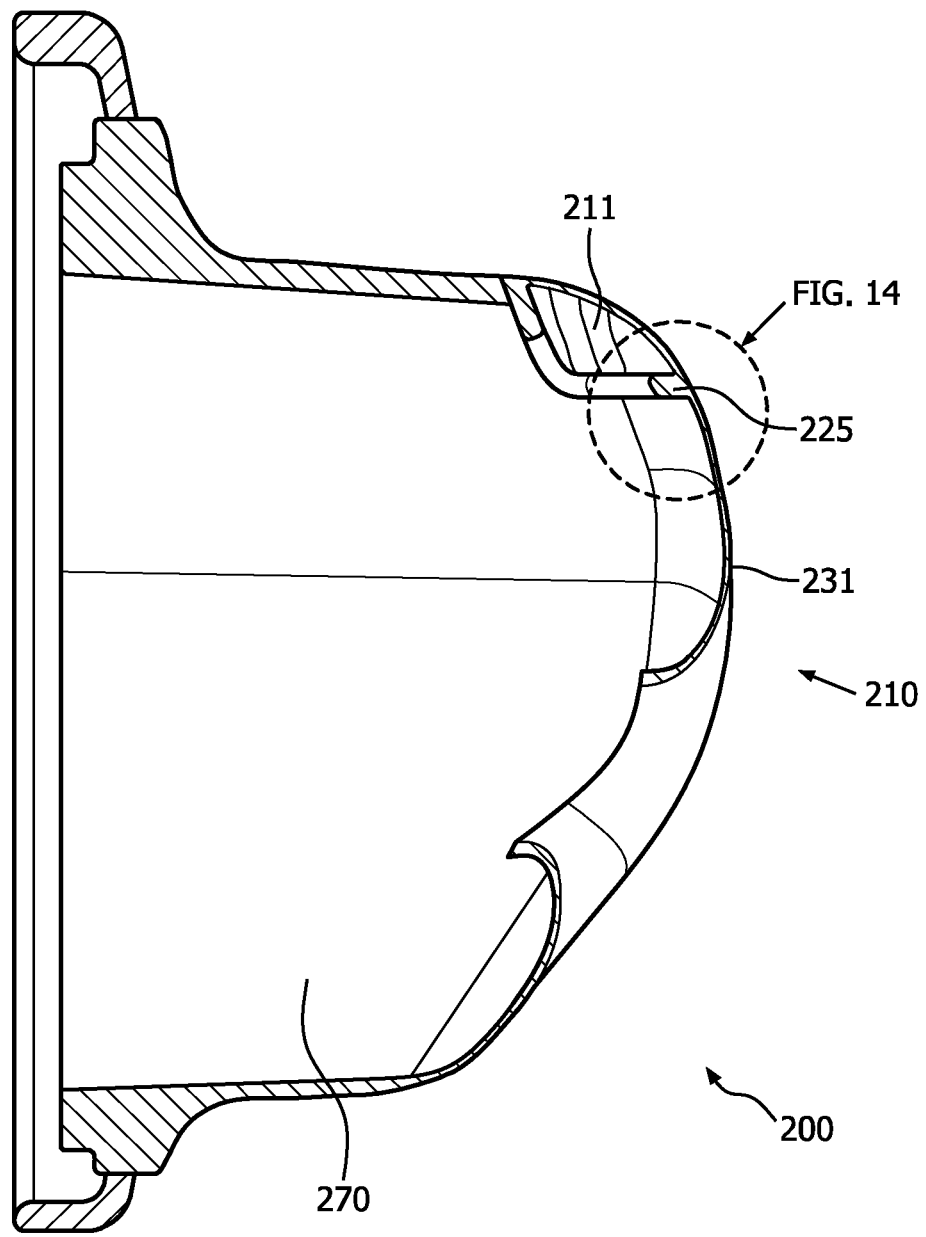
FIG. 13 is a section view of the cushion member of FIG. 11, taken along line C-C of FIG. 11.
Figure 14:
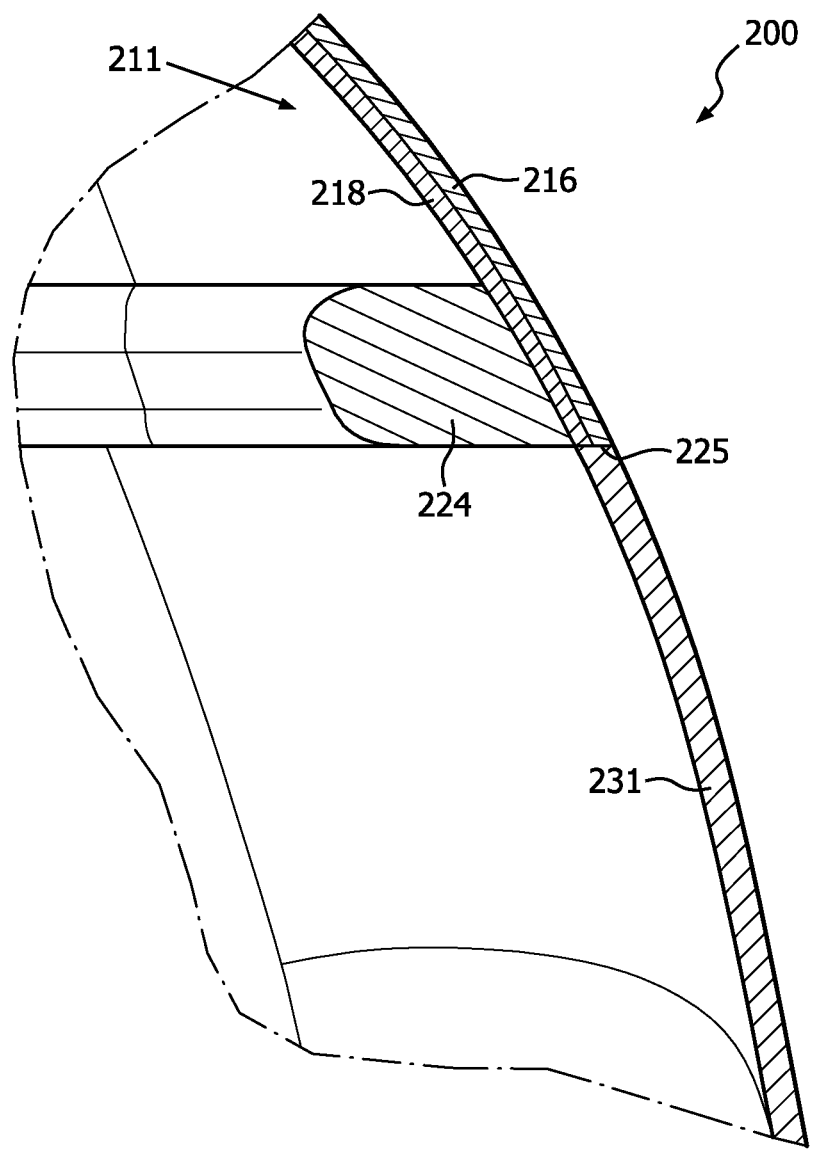
FIG. 14 is an enlarged view of a portion of the cushion member of FIG. 13.

FIG. 13 shows a section view of cushion member 200 and FIG. 14 shows an enlarged view of a portion of FIG. 13. Referring to FIG. 14, first flap portion 211 has a first layer 216 and a second layer 218 mechanically bonded to first layer 216. First layer 216 and second layer 218 are constructed of the same materials as, and are mechanically bonded in the same manner as, first and second layers 116,118, respectively, of cushion member 100, discussed hereinabove. Second flap portion 231, which extends from base portion 270, is made of a monomer, a polymer, or a mixture of a monomer and a polymer (e.g., without limitation, silicone). Second flap portion 231 is mechanically bonded to first layer 216 of first bonding portion 225 and chemically bonded to second layer 218 of first bonding portion 225 in order to connect second flap portion 231 to first bonding portion 225. Similarly, second flap portion 231 is mechanically bonded to first layer 216 of second bonding portion 226 and chemically bonded to second layer 218 of second bonding portion 226 in order to connect second flap portion 231 to second bonding portion 226. This particular manufacturing process creates an additional portion 227 proximate a nose bridge portion 212 of flap portion 211. Additional portion 227 requires extraction prior to use in pressure support therapy.

The composite nature of sealing portion 210 (i.e., employing first flap portion 211 and second flap portion 231) advantageously affords substantially similar advantages as sealing portion 110, discussed above, and additionally allows for increased friction between certain locations of the face of patient 14 and cushion member 200. More specifically, cushion member 200 is structured to have increased flexibility proximate nose bridge portion 212 (FIGS. 10-12) as a result of the material nature of first flap portion 211. Additionally, because patients often move their mouths during the night, it is desirable for full face cushion members, such as cushion member 200, to have increased friction between the patient and the cushion member proximate the mouth region in order to prevent the seal portion from entering the patient's mouth. As a result, cushion member 200 advantageously addresses this issue by having second flap portion 231 be different than first flap portion 211. More specifically, second flap portion 231 is made of a monomer, a polymer, or a mixture of a monomer and a polymer, and has a relatively large coefficient of friction (i.e., larger than first layer 216), thereby increasing friction between the mouth region of patient 14 and cushion member 200.

It will be appreciated that in both cushion member 100 and cushion member 200, base portions 170,270 are injection molded. In cushion member 100, base portion 170 is chemically bonded to second layer 118 by a lap-joint. Cushion member 200 includes a butt-joint to allow base portion 270 and second flap portion 231 to be chemically bonded to second layer 218.

Figure 15:
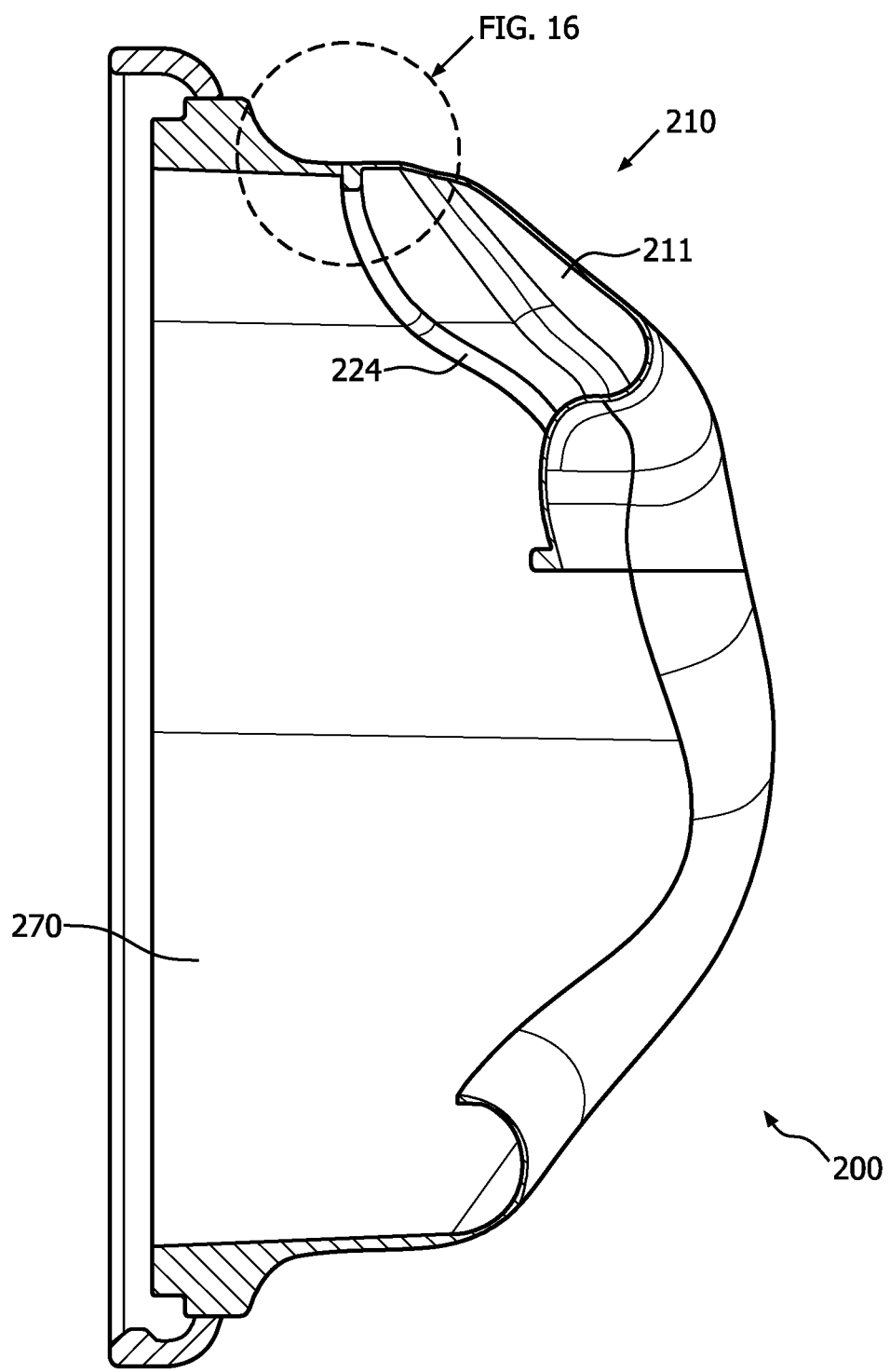
FIG. 15 is another section view of the cushion member of FIG. 11, taken along line D-D of FIG. 11.
Figure 16:
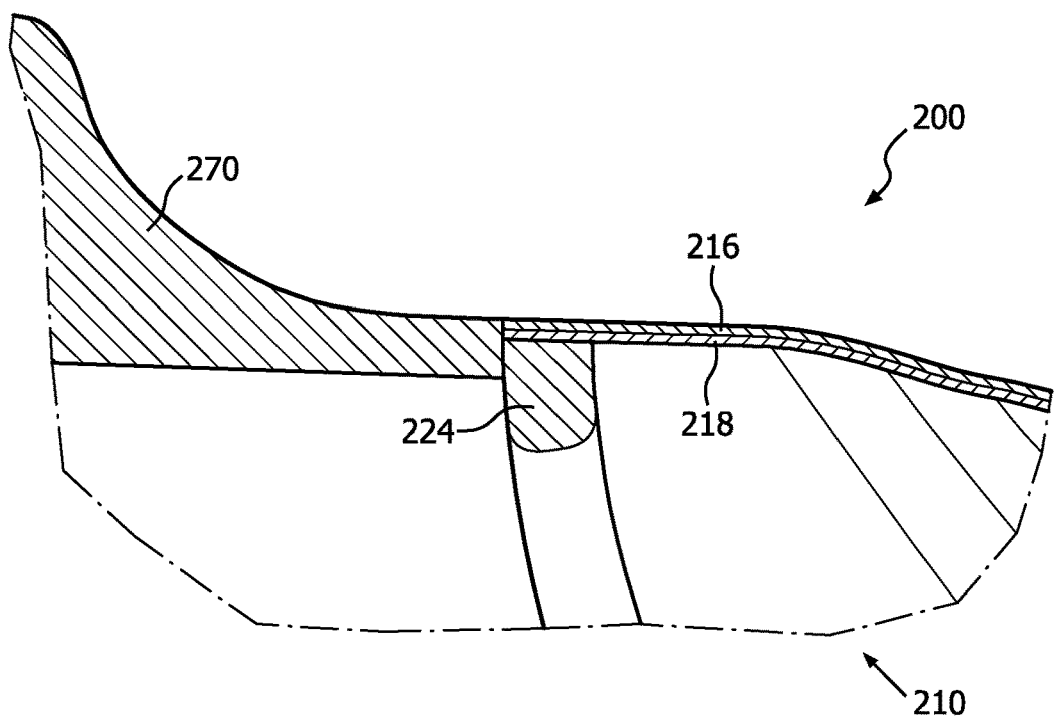
FIG. 16 is an enlarged view of a portion of the cushion member of FIG. 15.
Figure 17:
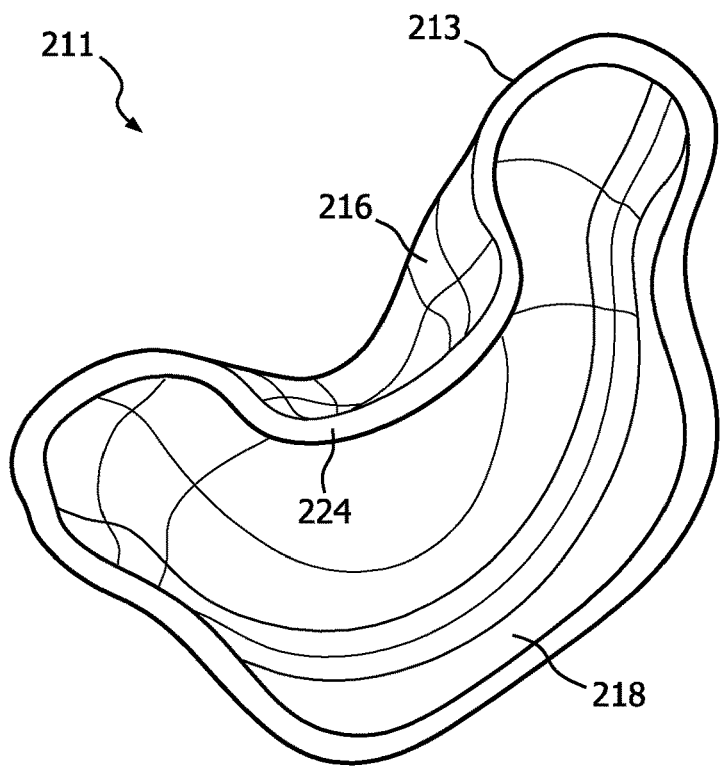
FIG. 17 is an isometric view of a flap portion of the cushion member of FIG. 11.

FIG. 15 shows another section view of cushion member 200 and FIG. 16 shows an enlarged view of a portion of FIG. 15. As shown in FIG. 16, sealing portion 210 further includes a bead 224 chemically bonded to base portion 270 and second layer 218. Referring to FIG. 17, first flap portion 211 has an outer edge 213 and bead 224 overlays (i.e., is located directly on top of) outer edge 213. Together, bead 224 and base portion 270 form the butt-joint. During manufacture of cushion member 200, bead 224 is first molded onto outer edge 213 in order to act as a shut off for when base portion 270 is molded. More specifically, once bead 224 is molded to second layer 218, a matching groove in the molding machine (not shown) receives bead 224 and shuts off on bead 224. It will be appreciated that the disclosed process advantageously allows for usage of relatively high injection pressures necessary for molding base portion 270 and second flap portion 231 without the wrinkling of fabric or bleed through of the molding material.

Although cushion member 200 has been described herein in association with sealing portion 210 including bead 224 to form the butt-joint between first flap portion 211, and second flap portion 231 and base portion 270, a similar suitable alternative cushion member (not shown) could employ a lap-joint similar to the lap-joint formed by bonding layer 172 and flap portion 111, discussed hereinabove. Similarly, it will be appreciated that a cushion member similar to cushion member 100 could alternatively employ a bead and associated butt-joint to bond a respective base portion to a respective flap portion, without departing from the scope of the disclosed concept. Furthermore, a similar suitable alternative cushion member (e.g., without limitation, cradle style or pillows style cushion member) may include a sealing portion similar to sealing portions 110,210 in order to provide the desired improvements in emotional connection with a patient interface device for a patient, without departing from the scope of the disclosed concept.

Additionally, a method of manufacturing cushion members 100,200 includes the steps of mechanically bonding first layer 116,216 to second layer 118,218, first layer 116,216 being structured to engage the face of patient 14 and being made of a fabric material, second layer 118,218 being made of a material selected from the group consisting of a monomer, a polymer, and a mixture of a monomer and a polymer, and chemically bonding base portion 170,270 to second layer 118,218. The method may further include the step of chemically bonding bead 224 to base portion 270 and second layer 218. Similarly, the method may also include the step of chemically bonding a bead similar to bead 224 to base portion 170 and second layer 118. The method of manufacturing cushion member 200 may further include the steps of: mechanically bonding second flap portion 231 to first layer 216 of first bonding portion 225 and first layer 216 of second bonding portion 226, and chemically bonding second flap portion 231 to second layer 218 of first bonding portion 225 and second layer 218 of second bonding portion 226.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A cushion member for a patient interface device, the cushion member comprising:
    a sealing portion comprising a flap portion including a first layer and a second layer mechanically bonded to the first layer, the first layer being structured to engage a face of a patient and being made of a fabric material, the second layer being made of a material selected from the group consisting of a monomer, a polymer, and a mixture of a monomer and a polymer; and
    a base portion bonded to the second layer, the base portion being structured to be coupled to a gas delivery conduit, wherein the flap portion has an outer edge and an inner edge, wherein the base portion comprises a bonding layer chemically bonded to a first side of the second layer to form a lap-joint, wherein a second side of the second layer at the lap-joint is mechanically bonded to the first layer such that the second layer is disposed between the first layer and the bonding layer at the lap-joint, and wherein the bonding layer is disposed between the outer edge and the inner edge,
    wherein the flap portion further has a nose bridge portion, a pair of opposing nasal transition portions each extending from the nose bridge portion, and a body portion connecting the nasal transition portions to one another, wherein the bonding layer extends inwardly from the outer edge of the nose bridge portion a first distance, and wherein the bonding layer extends inwardly from the outer edge of the body portion a second distance greater than the first distance such that the lap-joint has a first length proximate the nose bridge portion and a second length proximate the body portion with the second length being greater than the first length.

2. The cushion member according to claim 1, wherein the bonding layer extends inwardly from the outer edge of the nasal transition portions a third distance greater than the first distance and the second distance.

3. The cushion member according to claim 1, wherein the second layer comprises a first portion and a second portion extending from the first portion, wherein the first portion is chemically bonded to the bonding layer, wherein the second portion is not chemically bonded to the bonding layer, and wherein the second portion is flat.

4. The cushion member according to claim 1, wherein the sealing portion further comprises a bead chemically bonded to the base portion and the second layer.

5. The cushion member according to claim 4, wherein the flap portion comprises an outer edge, and wherein the bead overlays the outer edge.

6. The cushion member according to claim 1, wherein the flap portion comprises a first bonding portion and a second bonding portion disposed opposite the first bonding portion, wherein the sealing portion further comprises a second flap portion made of a material selected from the group consisting of a monomer, a polymer, and a mixture of a monomer and a polymer, wherein the second flap portion is mechanically bonded to the first layer of the first bonding portion and chemically bonded to the second layer of the first bonding portion, and wherein the second flap portion is mechanically bonded to the first layer of the second bonding portion and chemically bonded to the second layer of the second bonding portion.

7. The cushion member according to claim 1, wherein the flap portion is not in a state of tension.

8. The cushion member according to claim 1, wherein the first layer has a density of between 100 and 350 grams per square meter.

9. The cushion member according to claim 1, wherein the second layer has a thickness of between 0.002 and 0.02 inches.

10. The cushion member according to claim 1, wherein the second layer partially extends into the first layer.

11. A method of manufacturing a cushion member for a patient interface device, the cushion member comprising a sealing portion and a base portion, the base portion being structured to be coupled to a gas delivery conduit, the sealing portion comprising a flap portion, the method comprising the steps of:
   mechanically bonding a first layer of the flap portion to a second layer of the flap portion, the first layer being structured to engage a face of a patient and being made of a fabric material, the second layer being made of a material selected from the group consisting of a monomer, a polymer, and a mixture of a monomer and a polymer; and
   bonding the base portion to the second layer, wherein the flap portion has an outer edge and an inner edge, wherein the base portion comprises a bonding layer chemically bonded to a first side of the second layer to form a lap-joint, wherein a second side of the second layer at the lap-joint is mechanically bonded to the first layer such that the second layer is disposed between the first layer and the bonding layer at the lap-joint, and wherein the bonding layer is disposed between the outer edge and the inner edge,
   wherein the flap portion further has a nose bridge portion, a pair of opposing nasal transition portions each extending from the nose bridge portion, and a body portion connecting the nasal transition portions to one another, wherein the bonding layer extends inwardly from the outer edge of the nose bridge portion a first distance, and wherein the bonding layer extends inwardly from the outer edge of the body portion a second distance greater than the first distance such that the lap-joint has a first length proximate the nose bridge portion and a second length proximate the body portion with the second length being greater than the first length.

12. The method according to claim 11, further comprising the step of bonding a bead to the base portion and the second layer.

13. The method according to claim 11, wherein the flap portion comprises a first bonding portion and a second bonding portion disposed opposite the first bonding portion, wherein the sealing portion further comprises a second flap portion made of a material selected from the group consisting of a monomer, a polymer, and a mixture of a monomer and a polymer, and wherein the method further comprises the steps of:
   mechanically bonding the second flap portion to the first layer of the first bonding portion and the first layer of the second bonding portion; and
   chemically bonding the second flap portion to the second layer of the first bonding portion and the second layer of the second bonding portion.

14. A patient interface device comprising:
   (a) a frame member;
   (b) a strap member coupled to the frame member; and
   (c) a cushion member coupled to the frame member, the cushion member comprising:
   (1) a sealing portion comprising a flap portion including a first layer and a second layer mechanically bonded to the first layer, the first layer being structured to engage a face of a patient and being made of a fabric material, the second layer being made of a material selected from the group consisting of a monomer, a polymer, and a mixture of a monomer and a polymer; and
   (2) a base portion bonded to the second layer, the base portion being structured to be coupled to a gas delivery conduit, wherein the flap portion has an outer edge and an inner edge, wherein the base portion comprises a bonding layer chemically bonded to a first side of the second layer to form a lap-joint, wherein a second side of the second layer at the lap-joint is mechanically bonded to the first layer such that the second layer is disposed between the first layer and the bonding layer at the lap-joint, and wherein the bonding layer is disposed between the outer edge and the inner edge,
   wherein the flap portion further has a nose bridge portion, a pair of opposing nasal transition portions each extending from the nose bridge portion, and a body portion connecting the nasal transition portions to one another, wherein the bonding layer extends inwardly from the outer edge of the nose bridge portion a first distance, and wherein the bonding layer extends inwardly from the outer edge of the body portion a second distance greater than the first distance such that the lap-joint has a first length proximate the nose bridge portion and a second length proximate the body portion with the second length being greater than the first length.

* * * * *